(12) United States Patent
Yang et al.

(10) Patent No.: US 11,049,223 B2
(45) Date of Patent: Jun. 29, 2021

(54) CLASS-AWARE ADVERSARIAL PULMONARY NODULE SYNTHESIS

(71) Applicant: Siemens Healthcare GmbH, Erlangen (DE)

(72) Inventors: Jie Yang, New York, NY (US); Siqi Liu, Princeton, NJ (US); Sasa Grbic, Plainsboro, NJ (US); Arnaud Arindra Adiyoso, Nuremberg (DE); Zhoubing Xu, Plainsboro, NJ (US); Eli Gibson, Plainsboro, NJ (US); Guillaume Chabin, Princeton, NJ (US); Bogdan Georgescu, Plainsboro, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 113 days.

(21) Appl. No.: 16/445,435

(22) Filed: Jun. 19, 2019

(65) Prior Publication Data

US 2020/0402215 A1    Dec. 24, 2020

(51) Int. Cl.
*G06K 9/00*    (2006.01)
*G06T 5/00*    (2006.01)
(Continued)

(52) U.S. Cl.
CPC ............ *G06T 5/005* (2013.01); *A61B 5/7267* (2013.01); *A61B 6/032* (2013.01); *A61B 6/12* (2013.01);
(Continued)

(58) Field of Classification Search
CPC . G06T 2207/10072; G06T 2207/10081; G06T 2207/10084; G06T 2207/10088; G06T 2207/10092; G06T 2207/10096; G06T 2207/10116; G06T 2207/10124; G06T 2207/10128; G06T 5/005; G06T 7/0012; G06T 2200/3004; G06T 2200/30096; G06T 15/00; G06T 15/08; A61B 5/00; A61B 5/72; A61B 5/7235;
(Continued)

(56) References Cited

U.S. PATENT DOCUMENTS

| 10,580,131 | B2 * | 3/2020 | Mazo | ..................... G16H 30/40 |
| 2008/0205717 | A1 * | 8/2008 | Reeves | ................... G06T 5/002 |
| | | | | 382/128 |

OTHER PUBLICATIONS

Wu et al., "Conditional Infilling GANs for Data Augmentation in Mammogram Classification", Image Analysis for Moving Organ, Breast, and Thoracic Images, Springer, Aug. 24, 2018, 8 pgs.
(Continued)

*Primary Examiner* — Duy M Dang

(57) ABSTRACT

Systems and methods are provided for generating a synthesized medical image patch of a nodule. An initial medical image patch and a class label associated with a nodule to be synthesized are received. The initial medical image patch has a masked portion and an unmasked portion. A synthesized medical image patch is generated using a trained generative adversarial network. The synthesized medical image patch includes the unmasked portion of the initial medical image patch and a synthesized nodule replacing the masked portion of the initial medical image patch. The synthesized nodule is synthesized according to the class label. The synthesized medical image patch is output.

20 Claims, 9 Drawing Sheets

(51) Int. Cl.
  A61B 5/00 (2006.01)
  A61B 6/03 (2006.01)
  A61B 6/12 (2006.01)
  G06T 7/00 (2017.01)
(52) U.S. Cl.
  CPC .. *G06T 7/0012* (2013.01); *G06T 2207/10081* (2013.01); *G06T 2207/20081* (2013.01); *G06T 2207/20084* (2013.01); *G06T 2207/30064* (2013.01)
(58) Field of Classification Search
  CPC ....... A61B 5/7264; A61B 5/7267; A61B 6/00; A61B 6/032; A61B 6/12; G16H 30/20; G06N 20/00; G06N 20/10; G06N 20/20; G06N 30/00; G06N 30/02; G06N 30/04; G06N 30/08; G06N 30/084; G06F 19/00; G06F 19/30
  See application file for complete search history.

(56) References Cited

OTHER PUBLICATIONS

Jin et al., "CT-Realistic Lung Nodule Simulation from 3D Conditional Generative Adversarial Networks for Robust Lung Segmentation", Jun. 11, 2018, 8 pgs.
Armato et al., "The Lung Image Database Consortium (LIDC) and Image Database Resource Initiative (IDRI): A Completed Reference Database of Lung Nodules on CT Scans", Medical Physics, vol. 38, No. 2, Feb. 2011.
Clark et al., "The Cancer Imaging Archive (TCIA): Maintaining and Operating a Public Information Repository", J Digit Imaging, 2013, Springer, pp. 1045-1057.
He et al., "Deep Residual Learning for Image Recognition", 2016 IEEE Conference on Computer Vision and Pattern Recognition, pp. 770-778.
Xie et al., "Aggregated Residual Transformations for Deep Neural Networks", 2017 IEEE Conference on Computer Vision and Pattern Recognition.
Armato III et al., "Data from LIDC-IDRI", 2015.
Liu et al., "Decompose to Manipulate: Manipulable Object Synthesis in 3D Medical Images with Structured Image Decomposition", Feb. 7, 2019, 8 pgs.
MacMahon et al., "Guidelines for Management of Small Pulmonary Nodules Detected on CT Scans: A Statement from the Fleischner Society", Radiology, 2005, pp. 395-400.
Setio et al., "Validation, Comparison, and Combination of Algorithms for Automatic Detection of Pulmonary Nodules in Computed Tomography Images: The LUNA16 Challenge", Medical Image Analysis, vol. 42, Dec. 2017, pp. 1-13.
Shin et al, "Deep Convolutional Neural Networks for Computer-Aided Detection: CNN Architectures, Dataset Characteristics and Transfer Learning", IEEE Transactions on Medical Imaging, vol. 35, No. 5, May 2016, pp. 1285-1298.
Carreira et al., "Quo Vadis, Action Recognition? A New Model and the Kinetics Dataset", IEEE Conference on Computer Vision and Pattern Recognition (CVPR), Feb. 12, 2018, 10 pgs.
Kay et al., "The Kinetics Human Action Video Dataset", May 19, 2017, 22 pgs.
Hara et al., "Can Spatiotemporal 3D CNNs Retrace the History of 2D CNNs and ImageNet?", InProceedings of the IEEE Conference on Computer Vision and Pattern Recognition, 2018, pp. 6546-6555.
Yu et al., "Generative Image Inpainting with Contextual Attention", IEEE, Jan. 24, 2018, pp. 5505-5514.
Choi et al., "StarGAN: Unitied Generative Adversarial Networks for Multi-Domain Image-to-Image Translation", Nov. 24, 2017, 15 pgs.
Arjovsky et al., "Wasserstein Generative Adversarial Networks", InInternational Conference on Machine Learning, Jul. 17, 2017, 10 pgs.
Gulrajani et al., "Improved Training of Wasserstein GANs", InAdvances in Neural Information Processing Systems, May 29, 2017, 19 pgs.
Yang et al., "Class-Aware Adversarial Lung Nodules Synthesis in CT Images", Dec. 28, 2018, 5 pgs.
Extended European Search Report (EESR) dated Oct. 9, 2020 in corresponding European Patent Application No. 20180533.0.
Yang, Jie et al: "Class-Aware Adversarial Lung Nodule Synthesis in CT Images"; 2019 IEEE 16th International Symposium on Biomedical Imaging (ISBI 2019); IEEE; Apr. 8, 2019; pp. 1348-1352.

* cited by examiner

Receiving 1) an initial medical image patch having a masked portion and an unmasked portion, and 2) a class label associated with a nodule to be synthesized
202

Generating a synthesized medical image patch using a trained generative adversarial network, the synthesized medical image patch comprising the unmasked portion of the initial medical image patch and a synthesized nodule replacing the masked portion of the initial medical image patch, the synthesized nodule being synthesized according to the class label
204

Outputting the synthesized medical image patch
206

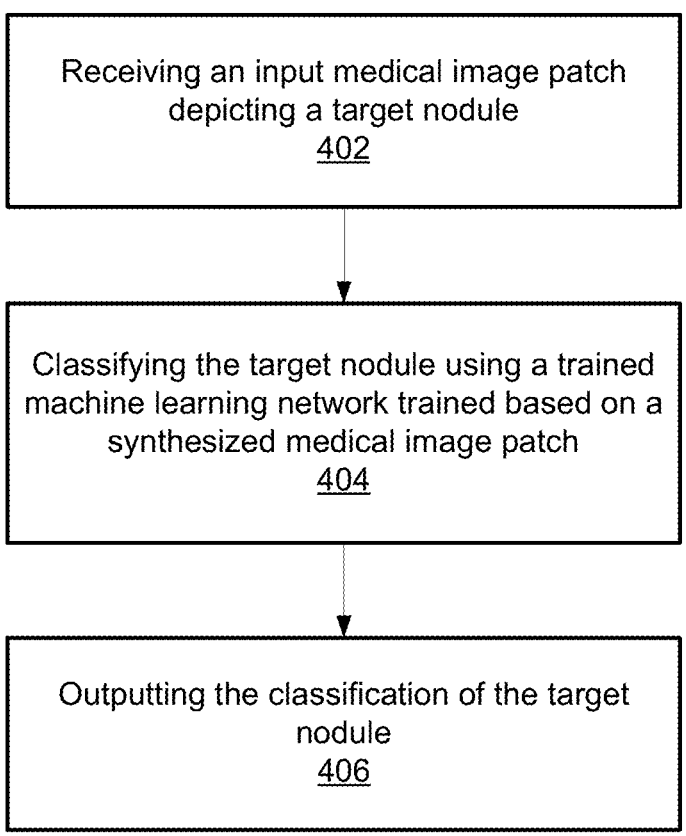

| Network | ACC | SEN | SPE | AUC |
|---|---|---|---|---|
| Raw | | | | |
| ResNet-50 | 0.8216 | 0.6666 | 0.8496 | 0.8286 |
| ResNet-101 | 0.8853 | 0.6666 | 0.9248 | 0.8320 |
| ResNet-152 | 0.8917 | 0.5833 | 0.9473 | 0.8756 |
| ResNext-101 | 0.9044 | 0.6249 | 0.9548 | 0.8558 |
| Mean | 0.8757 | 0.6353 | 0.9191 | 0.8480 |
| Raw + Weighted Loss | | | | |
| ResNet-50 | 0.8662 | 0.6666 | 0.9022 | 0.8161 |
| ResNet-101 | 0.7961 | 0.7499 | 0.8045 | 0.8154 |
| ResNet-152 | 0.8598 | 0.7083 | 0.8872 | 0.8098 |
| ResNext-101 | 0.8471 | 0.6666 | 0.8796 | 0.8342 |
| Mean | 0.8423 | 0.6978 | 0.8683 | 0.8188 |
| Raw + Synthesis | | | | |
| ResNet-50 | 0.8216 | 0.7083 | 0.8421 | 0.8746 |
| ResNet-101 | 0.9044 | 0.5833 | 0.9624 | 0.8458 |
| ResNet-152 | 0.9171 | 0.5833 | 0.9774 | 0.8812 |
| ResNext-101 | 0.8853 | 0.6666 | 0.9248 | 0.8768 |
| Mean | 0.8821 | 0.6353 | 0.9266 | 0.8696 |

CLASS-AWARE ADVERSARIAL PULMONARY NODULE SYNTHESIS

TECHNICAL FIELD

The present invention relates generally to class-aware adversarial pulmonary nodule synthesis, and more particularly to synthesizing pulmonary nodule image patches depicting benign or malignant nodules according to a user defined class label using a generative adversarial network (GAN).

BACKGROUND

Pulmonary nodules are a crucial indicator of early stage lung cancer. In the current clinical practice, lung cancer screening is performed by identifying nodules in computed tomography (CT) images. However, the vast majority of nodules are determined to be benign.

Deep convolutional neural networks (CNNs) have been demonstrated to perform well for image related tasks such as, for example, image segmentation, object detection, and classification. Deep CNNs have been proposed for pulmonary nodule detection and classification. However the performance of such deep CNN-based pulmonary nodule detection and classification methods are constrained by the quantity and the diversity of available training data. Since the vast majority of real world training data is of benign nodules, the cancerous cases of malignant modules are generally underrepresented in the training data. Moreover, the complexity of individual nodules resides in both their diverse appearance and physiological context, which is difficult to capture with such limited training data. The collection and annotation of large radiology image datasets are also time consuming and expensive tasks, and the resultant dataset may still lack representations from various nodule morphologies and sizes.

In one conventional approach, generative adversarial networks (GANs) were proposed to synthesize lesions in medical image patches to augment training data. However, such networks were designed to generate objects conditioned based on only the surrounding context and random noises, and lack the capability of generating objects with manipulable properties, such as benign or malignant, which are important for many machine learning applications in medical imaging.

BRIEF SUMMARY OF THE INVENTION

In accordance with one or more embodiments, systems and methods are provided for generating a synthesized medical image patch of a nodule. An initial medical image patch and a class label associated with a nodule to be synthesized are received. The initial medical image patch has a masked portion and an unmasked portion. A synthesized medical image patch is generated using a trained generative adversarial network. The synthesized medical image patch includes the unmasked portion of the initial medical image patch and a synthesized nodule replacing the masked portion of the initial medical image patch. The synthesized nodule is synthesized according to the class label. The synthesized medical image patch is output.

In one embodiment, the class label defines the synthesized nodule as being one of a synthesized malignant nodule or a synthesized benign nodule. Accordingly, the synthesized medical image patch includes the unmasked portion of the initial medical image patch and the one of the synthesized malignant nodule or the synthesized benign nodule replacing the masked portion of the initial medical image patch generated according to the class label.

In one embodiment, the initial medical image patch initially depicts an existing nodule. The masked portion of the initial medical image patch masks the existing nodule.

In one embodiment, the synthesized medical image patch is generated by generating a coarse medical image patch from the initial medical image patch using a coarse generator of the generative adversarial network and generating the synthesized medical image patch from the generated coarse medical image patch using a refinement generator of the generative adversarial network. The refinement generator may be trained with adversarial loss based on a comparison between a synthesized training medical image patch and a real medical image patch, and with class-aware loss based on a classification of the synthesized training medical image patch.

In one embodiment, a machine learning network (e.g., a deep convolutional neural network) for classifying a target nodule in an input medical image patch is trained based on the synthesized medical image patch. Accordingly, the input medical image patch depicting the target nodule may be received, the target nodule may be classified as one of malignant or benign using the trained machine learning network, and the classification of the target nodule may be output.

These and other advantages of the invention will be apparent to those of ordinary skill in the art by reference to the following detailed description and the accompanying drawings.

BRIEF DESCRIPTION OF THE DRAWINGS

FIG. 2 shows a method for generating a synthesized medical image patch of a nodule, in accordance with one or more embodiments;

FIG. 4 shows a method for classifying a target nodule using a machine learning network trained using a synthesized medical image patch, in accordance with one or more embodiments;

FIG. 8 a table comparing results of different 3D convolutional neural network architectures trained in accordance with embodiments of the invention.

DETAILED DESCRIPTION

The present invention generally relates to class-aware adversarial pulmonary nodule synthesis. Embodiments of the present invention are described herein to give a visual understanding of methods for class-aware adversarial pulmonary nodule synthesis. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Further, it should be understood that while the embodiments discussed herein may be discussed with respect to generating synthesized medical image patches of a pulmonary nodule, the present invention is not so limited. Embodiments of the present invention may be applied for generating a synthesized image of any type and depicting any object of interest.

Figure 1:
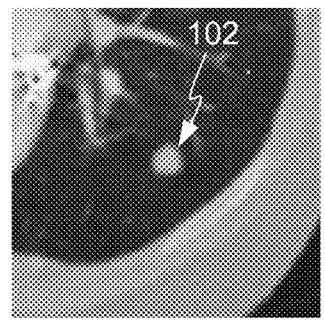
FIG. 1 shows an exemplary computed tomography medical image of a patient showing a malignant pulmonary nodule.

FIG. 1 shows an exemplary computed tomography (CT) medical image 100 of a patient showing pulmonary nodule 102. Pulmonary nodule 102 in image 100 is a malignant pulmonary nodule. Image 100 may be part of a training dataset for training a machine learning network for performing an image analysis task such as, e.g., classifying a nodule as benign or malignant. The vast majority of pulmonary nodules identified in CT medical images of a patient are determined to be benign. Accordingly, images of malignant pulmonary nodules are underrepresented in a typical training dataset.

Embodiments of the present invention provide for generating a synthesized medical image patch of a nodule to, e.g., augment real images in a training dataset for training a machine learning network. Such synthesized medical image patches may address the imbalance of a training dataset due to the relatively large amount of benign pulmonary nodule images available and the relatively small amount of malignant pulmonary nodule images available. Embodiments of the present invention formulate medical image patch synthesis as an in-painting problem by synthesizing a pulmonary nodule in a masked portion of a 3D pulmonary CT image of a patient. The synthesized pulmonary nodule may be generated according to user defined manipulable properties, such as, e.g., malignant or benign. Embodiments of the present invention synthesize the pulmonary nodule images according to a two component framework: 1) two generators to perform course-to-fine in-painting by incorporating contextual information; and 2) local and global discriminators to enforce the local quality and the global consistency of the generated patches and auxiliary domain classifiers to constrain the synthesized pulmonary nodules to manipulable properties. Such synthesized medical image patches of a nodule may augment real images in a training dataset for training a machine learning network for pulmonary nodule classification (or any other image analysis task).

FIG. 2 shows a method 200 for generating a synthesized medical image patch of a nodule, in accordance with one or more embodiments. The steps of method 200 may be performed by a computing device, such as, e.g., computer 902 of FIG. 9.

At step 202, an initial medical image patch and a class label associated with a nodule to be synthesized are received. In one embodiment, the initial medical image patch is a 3D computed tomography (CT) medical image patch, however the initial medical image patch of any suitable modality, such as, e.g., DynaCT, x-ray, magnetic resonance imaging (MRI), ultrasound (US), single-photon emission computed tomography (SPECT), positron emission tomography (PET), etc., and may be two dimensional or three dimensional.

The initial medical image patch may be extracted from a medical image using any suitable approach. In one embodiment, an existing nodule is annotated (e.g., manually by a user or automatically) on the medical image and the initial medical image patch is extracted from the medical image centered on the annotated existing nodule. In another embodiment, the initial medical image patch may be extracted at a randomly determined location or a user selected location on the medical image. The initial medical image patch may be of any suitable (e.g., predetermined) dimension. For example, the initial medical image patch may be a 64×64×32 voxel patch extracted from a 3D CT medical image (or a 64×64 pixel patch extracted from a 2D CT medical image). In another example, the initial medical image patch is the entire medical image.

The initial medical image patch may include a mask channel to provide a masked portion and an unmasked portion of the initial medical image patch. In one embodiment, an existing nodule initially depicted in the initial medical image patch is replaced with a 3D spherical mask (or a 2D circular mask where the initial medical image patch is 2D) such that the masked portion covers the existing nodule. It should be understood that the mask may be of any suitable shape and dimension. For example, the 3D spherical mask may have a diameter that is equal to the annotated diameter of the existing nodule initially depicted in the initial medical image patch. In another embodiment, a mask may be placed at a random or a user selected location of the initial medical image patch. In one embodiment, the mask is a random noise mask such as, e.g., a Gaussian noise mask.

Figure 3A:
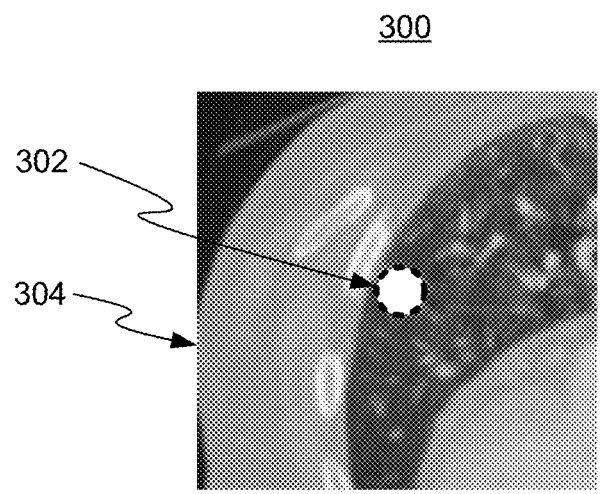
FIG. 3A shows an exemplary initial medical image patch, in accordance with one or more embodiments.

An exemplary initial medical image patch 300 is shown in FIG. 3A in accordance with one or more embodiments. Initial medical image patch 300 is a 2D CT medical image patch having masked portion 302 and unmasked portion 304. Unmasked portion 304 is defined as all portions of the initial medical image patch 300 outside of the masked portion 302.

The class label associated with a nodule to be synthesized defines any property associated with the nodule to be synthesized. In one embodiment, the class label defines the nodule to be synthesized as being one of a malignant nodule or a benign nodule. Any other property associated with the nodule to be synthesized may be defined by the class label. For example, the class label may define the nodule to be synthesized as being solid, part-solid, ground glass opacity, and calcification. The class label may be in any suitable format. In one example, the class label may be defined as 0 for a benign nodule and 1 for a malignant nodule.

At step 204, a synthesized medical image patch is generated using a trained generative adversarial network (GAN). Any other suitable machine learning network may additionally or alternatively be employed. The synthesized medical image patch comprises the unmasked portion of the initial medical image patch and a synthesized nodule replacing the masked portion of the initial medical image patch. The masked portion (e.g., random noise mask) causes varying shapes and textures of the synthesized nodule. The synthesized nodule is synthesized according to the class label. For example, in one embodiment, the synthesized nodule is a synthesized benign nodule where the class label defines the nodule as being benign and a synthesized malignant nodule where the class label defined the nodule as being malignant.

Figure 3B:
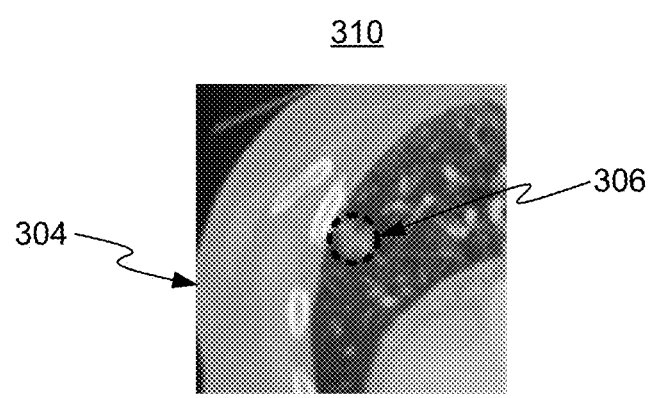
FIG. 3B shows an exemplary synthesized medical image patch, in accordance with one or more embodiments.

An exemplary synthesized medical image patch 310 is shown in FIG. 3B in accordance with one or more embodiments. Synthesized medical image patch 310 comprises unmasked portion 304 of initial medical image patch 300 and a synthesized nodule portion 306 replacing masked portion 302 (not shown in FIG. 3B) of the initial medical image patch 300. Synthesized nodule portion 306 is synthesized as a malignant module in synthesized medical image patch 310 in accordance with the class label. In some embodiments, an entirely new synthesized medical image patch 310 may be generated by generating synthesized nodule portion 306 and regenerating unmasked portion 304, while in other embodiments synthesized medical image patch 310 is generated by only generating synthesized nodule portion 306 while copying the imaging data of unmasked portion 304 from initial medical image patch 300.

In one embodiment, the trained GAN comprises a stacked image in-painting generator G formed of a coarse generator $G_1$ and a refinement generator $G_2$. Accordingly, the initial medical image patch and the class label are fed into coarse generator $G_1$ to generate a coarse medical image patch, which is fed into refinement generator $G_2$ to generate the synthesized medical image patch. Coarse generator $G_1$ is designed to be easier to optimized than refinement generator $G_2$. Coarse generator $G_1$ and refinement generator $G_2$ are both trained or optimized with a reconstruction loss $L_{recon}$ between the synthesized training medical image patch and the initial training medical image patch. Refinement generator $G_2$ is also trained with an adversarial approach using a local discriminator network $D_{local}$ and a global discriminator network $D_{global}$, which each incorporate an auxiliary domain classifier $D_{cls}$ to train generator G to generate a nodule according to the class label. The GAN is further described below with respect to FIG. 5, in accordance with one embodiment.

At step 206, the synthesized medical image patch is output. For example, the synthesized medical image patch can be output by displaying the synthesized medical image patch on a display device of a computer system (computer 902 of FIG. 9), storing the synthesized medical image patch on a memory or storage of a computer system (computer 902 of FIG. 9), or by transmitting the synthesized medical image patch to a remote computer system. In one embodiment, the synthesized medical image patch is output to a database as part of a training dataset for training a machine learning model.

It should be understood that method 200 may be repeatedly for any number of initial medical image patches to generate a plurality of synthesized medical image patches. The plurality of synthesized medical image patches may be used to, e.g., augment a training dataset of real medical image patches. For example, the plurality of synthesized medical image patches may be used to balance a training dataset of real medical image patches that have a relatively large amount of benign medical image patches and a relatively small amount of malignant medical image patches.

In one embodiment, the synthesized medical image patch may be used as part of a training dataset to train a machine learning network for classifying pulmonary nodules (or for performing any other image analysis task, such as, e.g., image segmentation or object detection). The machine learning network may be any suitable machine learning network. In one embodiment, the machine learning network is a deep 3D convolutional neural network (CNN) pre-trained for natural video classification. The machine learning network may be trained during an offline or training stage to perform the image analysis task (e.g., classifying pulmonary nodules) and applied during an online or testing stage to perform the image analysis task. The machine learning network may be trained using the synthesized medical image patch as is known in the art. The machine learning network may be applied during a testing stage according to method 400 for classifying a target nodule shown in FIG. 4.

At step 402 of FIG. 4, an input medical image patch depicting a target nodule is received. The input medical image patch may be of any suitable modality, but in one embodiment, is a 3D CT medical image patch. The input medical image patch may be extracted from an input medical image. For example, the target nodule may be annotated on the input medical image (e.g., manually by a user or automatically) and the input medical image patch is extracted from the input medical image centered on the annotated target nodule. The input medical image patch may be of any suitable dimension.

At step 404, the target nodule is classified using a trained machine learning network trained based on a synthesized medical image patch. The target nodule may be classified as one of malignant or benign. In one embodiment, the trained machine learning network is a deep 3D CNN pre-trained for natural video classification, however any suitable machine learning network may be employed. In one embodiment, the synthesized medical image patch is generated according to the steps of method 200 of FIG. 2.

At step 406, the classification of the target nodule is output. For example, the classification of the target nodule can be output by displaying the classification of the target nodule on a display device of a computer system (computer 902 of FIG. 9), storing the classification of the target nodule on a memory or storage of a computer system (computer 902 of FIG. 9), or by transmitting the classification of the target nodule to a remote computer system.

Figure 5:
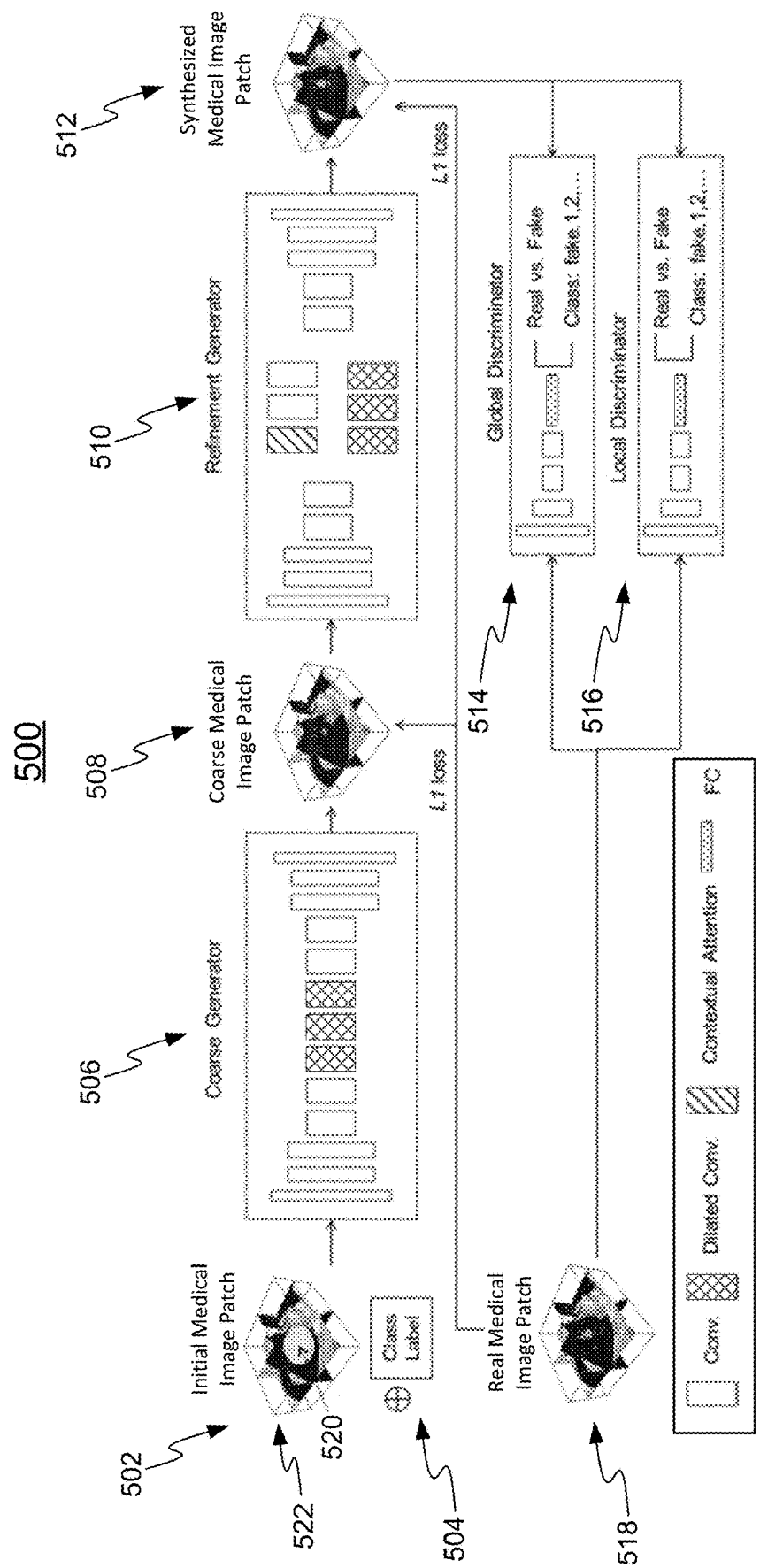
FIG. 5 shows a network architecture of a generative adversarial network trained for generating a synthesized medical image patch, in accordance with one or more embodiments.

FIG. 5 shows a network architecture of a GAN 500 for generating a synthesized medical image patch, in accordance with one or more embodiments. In one embodiment, GAN 500 of FIG. 5 is the trained GAN applied at step 204 of FIG. 2.

GAN 500 comprises a stacked image in-painting generator G formed of a coarse generator $G_1$ 506 and a refinement generator $G_2$ 510. During an online or testing stage of GAN 500, coarse generator $G_1$ 506 receives as input an initial medical image patch 502 and a class label 504. Initial medical image patch 502 has a masked portion 520 (e.g., masking an existing nodule initially depicted in initial medical image patch 502) and an unmasked portion 522. Class label 504 defines properties associated with a nodule to be synthesized, such as, e.g., malignant or benign. Coarse generator $G_1$ 506 generates a coarse medical image patch 508 according to class label 504. Coarse medical image patch 508 comprises the unmasked portion 522 of the initial medical image patch 502 and a coarsely synthesized nodule replacing the masked portion 520 of initial medical image patch 502. Coarse medical image patch 508 is fed into refinement generator $G_2$ 510 to refine the details of the coarsely synthesized nodule of coarse medical image patch 508 to generate synthesized medical image patch 512. Synthesized medical image patch 512 comprises the unmasked portion 522 of initial medical image patch 502 and a refined synthesized nodule replacing the masked portion 520 of initial medical image patch 502.

Coarse generator $G_1$ 506 and refinement generator $G_2$ 510 are formed from an encoder-decoder CNN having a number of convolutional layers and dilated convolutional layers. However, as shown in FIG. 5, refinement generator $G_2$ 510 also comprises a contextual attention layer (or model), which takes into account features from surrounding regions for in-painting the boundary of the synthesized nodule in synthesized medical image patch 512. The contextual attention layer matches the foreground and background textures by measuring the normalized inner product (cosine similarity) of their features. The similarity is weighed to determine an attention score for each surrounding voxel. An attention map on the background voxels is obtained for reconstructing the foreground area with the attention filtered background features by performing deconvolution on the attention score. The contextual attention layer is differentiable and fully-convolutional.

During an offline or training stage, coarse generator $G_1$ 506 and refinement generator $G_2$ 510 of GAN 500 are both trained or optimized with a reconstruction loss $L_{recon}$ between the synthesized training medical image patch and the initial training medical image patch. Reconstruction loss $L_{recon}$ for both coarse generator $G_1$ 506 and refinement generator $G_2$ 510 is expressed as Equation (1).

$$L_{recon}^{(1,2)} = L_{masked} + \lambda_1 L_{global} \quad (1)$$

where $L_{masked}$ and $L_{global}$ are the normalized L1 loss across the masked area and the entire patch, respectively. By optimizing $L_{recon}$, the stacked generator G is trained to reconstruct the nodules in the original patch based on the tissue context, the mask, and class label 504.

In addition to $L_{recon}$, refinement generator $G_2$ 510 is also trained by an adversarial loss process provided by a local discriminator network 516 and a global discriminator network 514. Local discriminator network 516 comprises an adversarial loss discriminator $D_{local}$ and global discriminator network 514 comprises an adversarial loss discriminator $D_{global}$. Discriminators $D_{local}$ and $D_{global}$ input the synthesized training medical image patch generated by refinement generator 510 and a real medical image patch 518 and classifies one image as real and the other image as fake (synthesized). Local adversarial loss discriminator $D_{local}$ is applied to the masked portion only to improve the appearance of the synthesized nodule. Global adversarial loss discriminator $D_{global}$ is applied to the entire patch for global consistency.

Both local adversarial loss discriminator $D_{local}$ and global adversarial loss discriminator $D_{global}$ will be denoted as $D^*$. Discriminators $D^*$ comprise a number of convolutional layers and fully convolution layers, as shown in FIG. 5. Using the conditional Wasserstein GAN objective and enforcing the gradient penalty to train the local and global discriminators $D^*$, stacked generator G and discriminators $D^*$ are expressed as the objective of Equation (2).

$$L_{adv} = E_x[D_*(x)] - E_{z,c}[D_*(G(x_{masked}, z, c))] - \lambda_{gp} E_{\hat{x}}[(\|\nabla D_*(\hat{x})\|_2 - 1)^2] \quad (2)$$

where x is sampled from real medical image patch 518, $G(x_{masked}, z, c)$ is the output of stacked generator G, and $\hat{x}$ is sampled uniformly between real patches and synthesized training patches. The class label c is replicated to the same size as the input training patch x and is concatenated with x as another input channel.

In addition to discriminators $D^*$, as auxiliary domain classifier $D_{cls}$ is added on top of each discriminator network 514 and 516 to ensure that stacked generator G generates nodules according to the targeted class c. In this training objective, each $D_{cls}$ attempts to classify the synthesized training medical image patch into the domain class c' (0=fake, 1=benign, and 2=malignant). The label 0 is used to prevent the generator form duplicating nodules that are easy to classify but less diversified. $D_{cls}$ is optimized with class-aware loss objective of Equation (3).

$$L_{cls} = E_{x,c'}[-\log D_{cls}(,c'|x)] \quad (3)$$

where $D_{cls}(,c'|x)$ represents a probability distribution over domain classes c'.

Though both $D^*$ and $D_{cls}$ are optimized to discriminate between fake and real patches, empirically it was found to be hard for the learning system to converge without $L_{adv}$. In practice, $L_{cls}$ may be added after the stacked generator G is well trained to in-paint real-looking nodules. In this adversarial learning problem, stacked generator G tried to in-paint the patch that can be classified as the target domain c as well as to fool $D^*$ to misjudge them in the distribution of the real patches. Discriminators $D^*$ and $D_{cls}$ are only used during the training stage, and is not used during the online or testing stage (e.g., to generated synthesized medical image patch 512).

The objective for the whole class-aware nodule synthesis learning can be summarized as Equations (4) and (5).

$$L_{D^*} = L_{adv} + \Delta_{cls}^{(D)} \quad (4)$$

$$L_G = L_{adv} + \lambda_{cls}^{(G)} L_{cls} + \lambda_{recon} L_{recon} \quad (5)$$

The embodiments described herein were evaluated on The Lung Image Database Consortium (LIDC-IDRI) dataset, comprising diagnostic and lung cancer screen thoracic CT scans with annotated lesions. The LIDC-IDRI dataset is formed from 1,010 patients and 1,308 chest CT imaging studies. The nodules in the LIDC-IDRI dataset were annotated by four radiologists. The likelihood of malignancy of each nodule was assessed, and a score ranging from 1 (highly unlikely) to 5 (highly suspicious) was given by each radiologist. The nodules with the majority score (i.e., 4) were defined to be malignant, and the rest benign. The patches were extracted from the LIDC-IDRI dataset with the resolution of 1×1×2 mm (i.e., 64×64×32 voxels). The patches were randomly split into a training set, a validation set, and a testing set.

The trained generator was used for synthesizing 463 patches depicting malignant patches from malignant patches randomly sampled from real training malignant patches, since malignant nodules are relatively rare in the LIDC-IDRI dataset. The synthesized patches are combined with the original training patches to train a 3D classification CNN.

Figure 6:
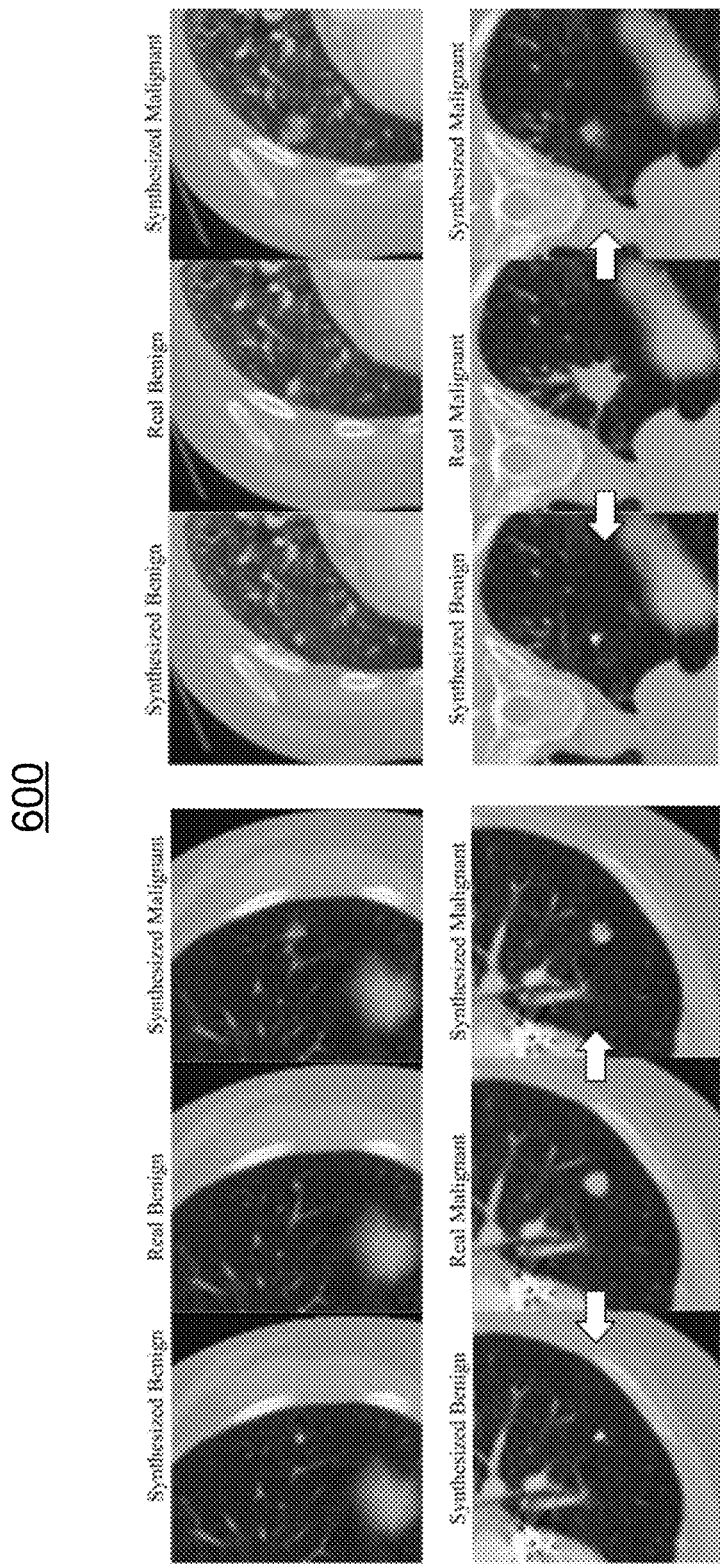
FIG. 6 shows a comparison of real initial medical image patches and synthesized medical image patches synthesized therefore in accordance with embodiments of the invention.

FIG. 6 shows a comparison 600 of real initial medical image patches and synthesized medical image patches synthesized therefrom in accordance with embodiments of the invention. Synthesized medical image patches are synthesized by altering the class label to benign or malignant. Given the same real patch, the embodiments described herein are capable of generating synthesized medical image patches having nodules with a different malignancy. As shown in FIG. 6, the synthesized benign nodules tend to have smaller sizes as well as clearly defined boundaries.

Figure 7:
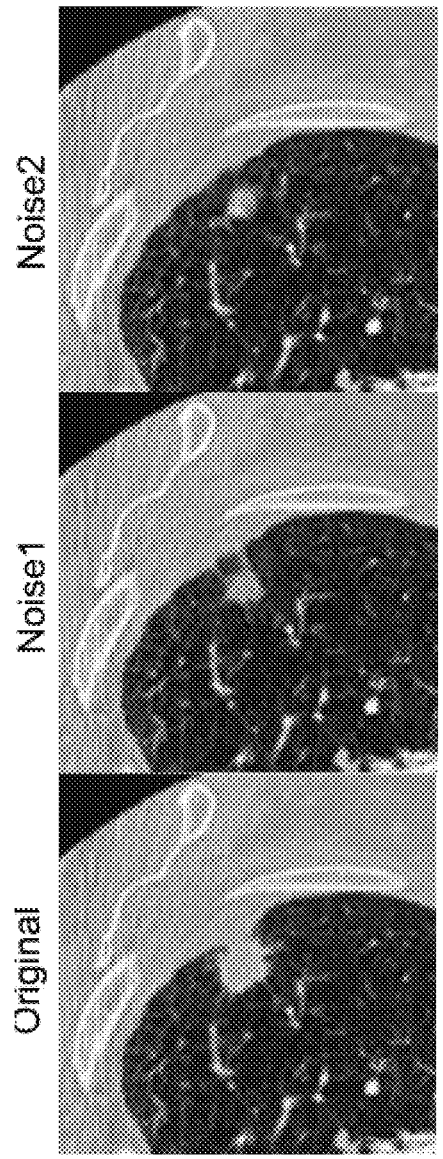
FIG. 7 shows a comparison of a real initial medical image patch and synthesized medical image patches synthesized according to different noise masks in accordance with embodiments of the invention.

FIG. 7 shows a comparison 700 of a real initial medical image patch and synthesized medical image patches synthesized according to different noise masks in accordance with embodiments of the invention. As shown in FIG. 7, different noise masks (labelled as Noise 1 and Noise 2) may result in synthesized nodules with different morphology and textures.

To evaluate the effectiveness of using the synthesized patches on classifying pulmonary nodules, four 3D CNN architectures were trained with different capacities: ResNet- 50, ResNet-101, ResNet-152, and ResNext-101. All networks were initialized with the weights pre-trained on the Kinetic video dataset. The cross-entropy loss was used for training the CNN classifiers. The differences between the unweighted (raw) and weighted cross entropy loss (raw+ weighted loss) were evaluated with the weights accounting for training sample class distribution. Traditional data augmentation methods including random cropping and scaling were used for training all networks. The testing accuracy (ACC), sensitivity (SEN), specific (SPE), and the area under the ROC curve (AUC) are presented in table 800 of FIG. 8. The models were selected based on the highest AUCs on the validation set. With the synthesized patches (Raw+Synthesized), the 3D ResNet-152 achieved the highest accuracy, specificity, and AUC score across all experiments. Though the weighted loss is typically used in the imbalanced dataset, it did not show better AUC than either the unweighted loss or the augmented dataset. The increase of the mean of the AUC scores also indicates that using the synthetic nodule patches are helpful for improving nodule malignancy classification performance.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 2 and 4. Certain steps or functions of the methods and workflows described herein, including one or more of the steps or functions of FIGS. 2 and 4, may be performed by a server or by another processor in a network-based cloud-computing system. Certain steps or functions of the methods and workflows described herein, including one or more of the steps of FIGS. 2 and 4, may be performed by a client computer in a network-based cloud computing system. The steps or functions of the methods and workflows described herein, including one or more of the steps of FIGS. 2 and 4, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 2 and 4, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 9:
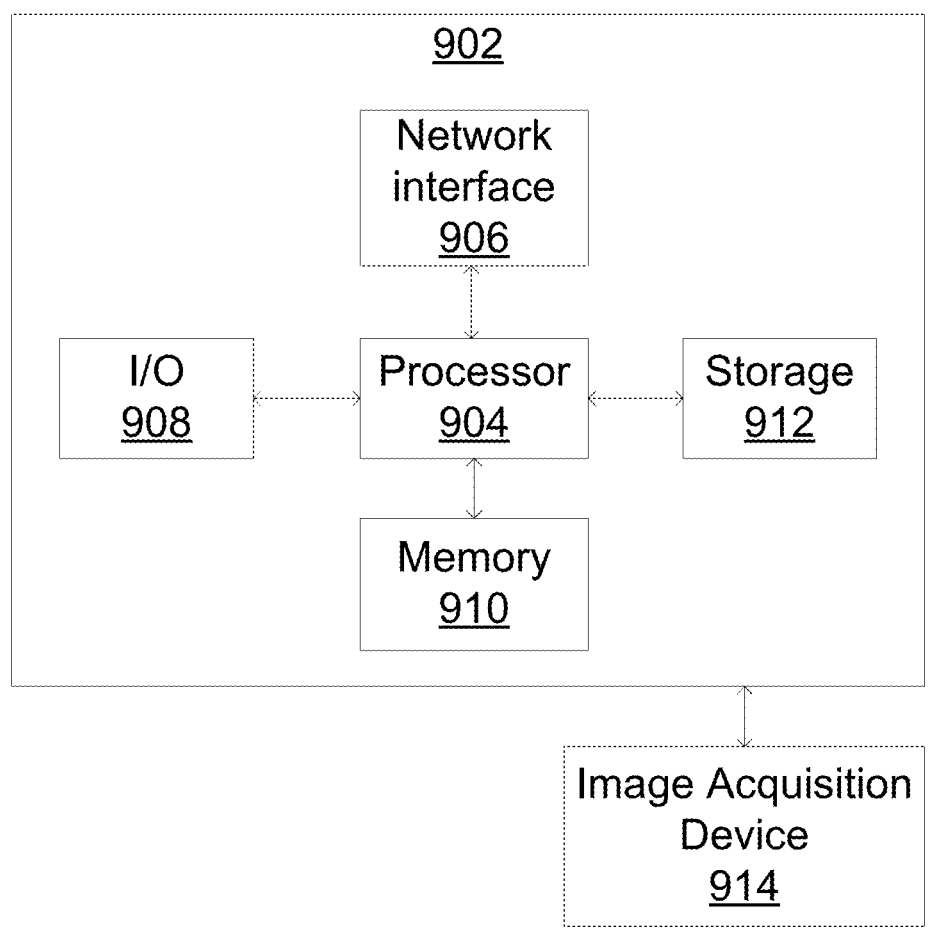
FIG. 9 shows a high-level block diagram of a computer.

A high-level block diagram of an example computer 902 that may be used to implement systems, apparatus, and methods described herein is depicted in FIG. 9. Computer 902 includes a processor 904 operatively coupled to a data storage device 912 and a memory 910. Processor 904 controls the overall operation of computer 902 by executing computer program instructions that define such operations. The computer program instructions may be stored in data storage device 912, or other computer readable medium, and loaded into memory 910 when execution of the computer program instructions is desired. Thus, the method and workflow steps or functions of FIGS. 2 and 4 can be defined by the computer program instructions stored in memory 910 and/or data storage device 912 and controlled by processor 904 executing the computer program instructions. For example, the computer program instructions can be implemented as computer executable code programmed by one skilled in the art to perform the method and workflow steps or functions of FIGS. 2 and 4. Accordingly, by executing the computer program instructions, the processor 904 executes the method and workflow steps or functions of FIGS. 2 and 4. Computer 902 may also include one or more network interfaces 906 for communicating with other devices via a network. Computer 902 may also include one or more input/output devices 908 that enable user interaction with computer 902 (e.g., display, keyboard, mouse, speakers, buttons, etc.).

Processor 904 may include both general and special purpose microprocessors, and may be the sole processor or one of multiple processors of computer 902. Processor 904 may include one or more central processing units (CPUs), for example. Processor 904, data storage device 912, and/or memory 910 may include, be supplemented by, or incorporated in, one or more application-specific integrated circuits (ASICs) and/or one or more field programmable gate arrays (FPGAs).

Data storage device 912 and memory 910 each include a tangible non-transitory computer readable storage medium. Data storage device 912, and memory 910, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 908 may include peripherals, such as a printer, scanner, display screen, etc. For example, input/output devices 908 may include a display device such as a cathode ray tube (CRT) or liquid crystal display (LCD) monitor for displaying information to the user, a keyboard, and a pointing device such as a mouse or a trackball by which the user can provide input to computer 902.

An image acquisition device 914 can be connected to the computer 902 to input image data (e.g., medical images) to the computer 902. It is possible to implement the image acquisition device 914 and the computer 902 as one device. It is also possible that the image acquisition device 914 and the computer 902 communicate wirelessly through a network. In a possible embodiment, the computer 902 can be located remotely with respect to the image acquisition device 914.

Any or all of the systems and apparatus discussed herein may be implemented using one or more computers such as computer 902.

One skilled in the art will recognize that an implementation of an actual computer or computer system may have other structures and may contain other components as well, and that FIG. 9 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for generating a synthesized medical image patch of a nodule, comprising:
receiving 1) an initial medical image patch having a masked portion and an unmasked portion, and 2) a class label associated with a nodule to be synthesized;
generating a synthesized medical image patch using a trained generative adversarial network, the synthesized medical image patch comprising the unmasked portion of the initial medical image patch and a synthesized nodule replacing the masked portion of the initial medical image patch, the synthesized nodule being synthesized according to the class label; and
outputting the synthesized medical image patch.

2. The method of claim 1, wherein the class label defines the synthesized nodule as being one of a synthesized malignant nodule or a synthesized benign nodule, and generating a synthesized medical image patch using a trained generative adversarial network comprises:
generating the synthesized medical image patch comprising the unmasked portion of the initial medical image patch and the one of the synthesized malignant nodule or the synthesized benign nodule replacing the masked portion of the initial medical image patch according to the class label.

3. The method of claim 1, wherein the initial medical image patch initially depicts an existing nodule and the masked portion of the initial medical image patch masks the existing nodule.

4. The method of claim 1, wherein generating a synthesized medical image patch using a trained generative adversarial network comprises:
generating a coarse medical image patch from the initial medical image patch using a coarse generator of the generative adversarial network; and
generating the synthesized medical image patch from the generated coarse medical image patch using a refinement generator of the generative adversarial network.

5. The method of claim 4, further comprising:
training the refinement generator with adversarial loss based on a comparison between a synthesized training medical image patch and a real medical image patch.

6. The method of claim 5, further comprising:
training the refinement generator with class-aware loss based on a classification of the synthesized training medical image patch.

7. The method of claim 1, further comprising:
training a machine learning network for classifying a target nodule in an input medical image patch based on the synthesized medical image patch.

8. The method of claim 1, further comprising:
receiving an input medical image patch depicting a target nodule;
classifying the target nodule as one of malignant or benign using a trained machine learning network trained based on the synthesized medical image patch; and
outputting the classification of the target nodule.

9. The method of claim 8, wherein the trained machine learning network is a trained deep convolutional neural network.

10. An apparatus, comprising:
means for receiving 1) an initial medical image patch having a masked portion and an unmasked portion, and 2) a class label associated with a nodule to be synthesized;
means for generating a synthesized medical image patch using a trained generative adversarial network, the synthesized medical image patch comprising the unmasked portion of the initial medical image patch and a synthesized nodule replacing the masked portion of the initial medical image patch, the synthesized nodule being synthesized according to the class label; and
means for outputting the synthesized medical image patch.

11. The apparatus of claim 10, wherein the class label defines the synthesized nodule as being one of a synthesized malignant nodule or a synthesized benign nodule, and the means for generating a synthesized medical image patch using a trained generative adversarial network comprises:
means for generating the synthesized medical image patch comprising the unmasked portion of the initial medical image patch and the one of the synthesized malignant nodule or the synthesized benign nodule replacing the masked portion of the initial medical image patch according to the class label.

12. The apparatus of claim 10, wherein the initial medical image patch initially depicts an existing nodule and the masked portion of the initial medical image patch masks the existing nodule.

13. The apparatus of claim 10, wherein the means for generating a synthesized medical image patch using a trained generative adversarial network comprises:
 means for generating a coarse medical image patch from the initial medical image patch using a coarse generator of the generative adversarial network; and
 means for generating the synthesized medical image patch from the generated coarse medical image patch using a refinement generator of the generative adversarial network.

14. The apparatus of claim 13, further comprising:
 means for training the refinement generator with adversarial loss based on a comparison between a synthesized training medical image patch and a real medical image patch.

15. The apparatus of claim 14, further comprising:
 means for training the refinement generator with class-aware loss based on a classification of the synthesized training medical image patch.

16. A non-transitory computer readable medium storing computer program instructions, the computer program instructions when executed by a processor cause the processor to perform operations comprising:
 receiving 1) an initial medical image patch having a masked portion and an unmasked portion, and 2) a class label associated with a nodule to be synthesized;
 generating a synthesized medical image patch using a trained generative adversarial network, the synthesized medical image patch comprising the unmasked portion of the initial medical image patch and a synthesized nodule replacing the masked portion of the initial medical image patch, the synthesized nodule being synthesized according to the class label; and
 outputting the synthesized medical image patch.

17. The non-transitory computer readable medium of claim 16, wherein the class label defines the synthesized nodule as being one of a synthesized malignant nodule or a synthesized benign nodule, and generating a synthesized medical image patch using a trained generative adversarial network comprises:
 generating the synthesized medical image patch comprising the unmasked portion of the initial medical image patch and the one of the synthesized malignant nodule or the synthesized benign nodule replacing the masked portion of the initial medical image patch according to the class label.

18. The non-transitory computer readable medium of claim 16, the operations further comprising:
 training a machine learning network for classifying a target nodule in an input medical image patch based on the synthesized medical image patch.

19. The non-transitory computer readable medium of claim 16, the operations further comprising:
 receiving an input medical image patch depicting a target nodule;
 classifying the target nodule as one of malignant or benign using a trained machine learning network trained based on the synthesized medical image patch; and
 outputting the classification of the target nodule.

20. The non-transitory computer readable medium of claim 19, wherein the trained machine learning network is a trained deep convolutional neural network.

* * * * *